United States Patent
Weasler et al.

(10) Patent No.: US 9,421,318 B2
(45) Date of Patent: Aug. 23, 2016

(54) BLOOD BAG SYSTEMS FOR SEPARATION OF WHOLE BLOOD AND METHODS OF USE THEREOF

(71) Applicant: FENWAL INC., Lake Zurich, IL (US)

(72) Inventors: Marc N. Weasler, West Bend, WI (US); Richard I. Brown, Northbrook, IL (US); Sean Ford, Carlsbad, CA (US); Mark J. Brierton, Cary, IL (US)

(73) Assignee: Fenwal, Inc., Lake Zurich, IL (US)

( * ) Notice: Subject to any disclaimer, the term of this patent is extended or adjusted under 35 U.S.C. 154(b) by 443 days.

(21) Appl. No.: 14/113,607

(22) PCT Filed: Oct. 24, 2012

(86) PCT No.: PCT/US2012/061592
§ 371 (c)(1),
(2) Date: Oct. 24, 2013

(87) PCT Pub. No.: WO2013/109327
PCT Pub. Date: Jul. 25, 2013

(65) Prior Publication Data
US 2014/0066281 A1 Mar. 6, 2014

Related U.S. Application Data

(60) Provisional application No. 61/586,985, filed on Jan. 16, 2012.

(51) Int. Cl.
*A61M 1/36* (2006.01)
*A61J 1/10* (2006.01)
(Continued)

(52) U.S. Cl.
CPC ............... *A61M 1/3693* (2013.01); *A61J 1/10* (2013.01); *A61J 1/16* (2013.01); *A61J 1/2093* (2013.01);
(Continued)

(58) Field of Classification Search
CPC B04B 5/0428; A61M 1/3693; A61M 1/0231; A61M 1/3698; A61M 1/0218; A61M 1/029; A61J 1/10; A61J 1/16; A61J 1/2093; A61J 1/12; A61J 1/2086; A61J 1/2034; A61J 1/2037
USPC ........................................................ 494/34, 37
See application file for complete search history.

(56) References Cited

U.S. PATENT DOCUMENTS 4,007,871 A 2/1977 Jones et al.
5,092,996 A 3/1992 Spielberg
(Continued)

FOREIGN PATENT DOCUMENTS

WO WO 2008002135 A1 * 1/2008 .......... A61M 1/0209

OTHER PUBLICATIONS

International Preliminary Report on Patentability mailed Jul. 31, 2014 in connection with PCT/US2012/061592.
(Continued)

*Primary Examiner* — Charles Cooley
*Assistant Examiner* — Shuyi S Liu
(74) *Attorney, Agent, or Firm* — Cook Alex Ltd.

(57) ABSTRACT

The present disclosure relates generally to systems for processing a unit of whole blood into its components while the unit is still in the centrifuge. The system comprises a container holding whole blood and one or more satellite bags or containers that are installed into a holder, which is then inserted into a bucket of the centrifuge. Tubes interconnect the containers, one or more of which are preferably installed into clamping mechanisms resident in the holder. The holder further preferably includes sensing means, such as optical sensors, to sense the location of the interfaces between the separated layers of the whole blood that result from rotation of the centrifuge.

10 Claims, 8 Drawing Sheets

(51) Int. Cl.
  *B04B 5/04* (2006.01)
  *A61J 1/16* (2006.01)
  *A61J 1/20* (2006.01)
  *A61M 1/02* (2006.01)
  *A61J 1/12* (2006.01)

(52) U.S. Cl.
  CPC ............ *A61M 1/0218* (2014.02); *A61M 1/0231* (2014.02); *A61M 1/3698* (2014.02); *B04B 5/0428* (2013.01); *A61J 1/12* (2013.01); *A61J 1/2034* (2015.05); *A61J 1/2037* (2015.05); *A61J 1/2086* (2015.05); *A61M 1/029* (2013.01)

(56) References Cited

U.S. PATENT DOCUMENTS

| | | | |
|---|---|---|---|
| 6,652,475 | B1 | 11/2003 | Sahines et al. |
| 6,910,998 | B2 | 6/2005 | Eberle |
| 7,094,197 | B2 | 8/2006 | Hlavinka et al. |
| 7,166,217 | B2 | 1/2007 | Holmes et al. |
| 2002/0020680 | A1 | 2/2002 | Jorgensen |
| 2003/0176267 | A1 | 9/2003 | Eberle |
| 2006/0068369 | A1 | 3/2006 | Coelho et al. |
| 2009/0286221 | A1* | 11/2009 | Klip .................... A61M 1/0209 435/2 |
| 2011/0301012 | A1* | 12/2011 | Dolecek .............. A61M 1/3693 494/10 |

OTHER PUBLICATIONS

European Patent Office, Supplementary European Search Report, counterpart EP Appl. No. 12866168, date of completion of search Sep. 11, 2015, 2 pages.

European Patent Office, Search Opinion, counterpart EP Appl. No. 12866168, date of completion of search Sep. 11, 2015, 2 pages.

\* cited by examiner

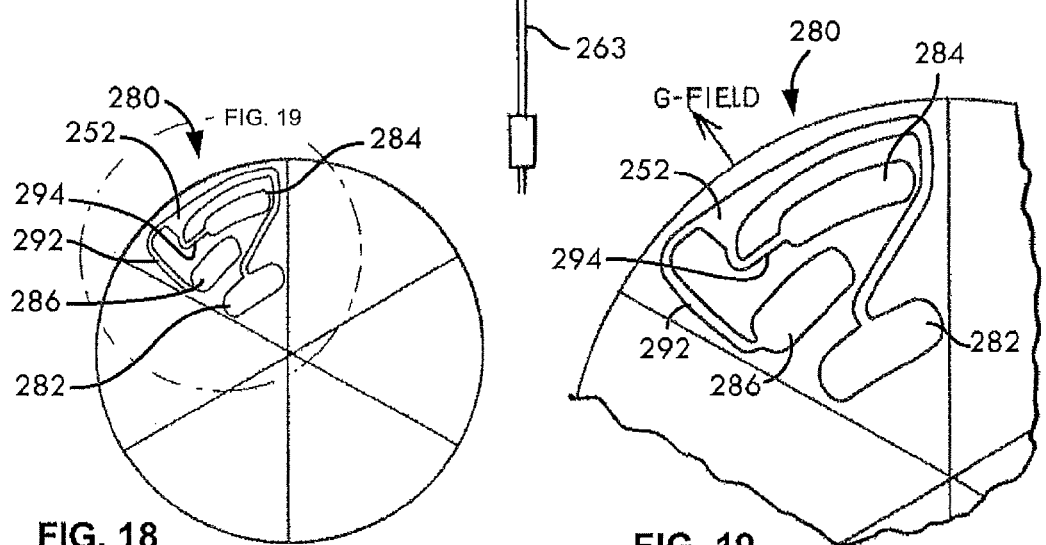
FIG. 17
FIG. 18
FIG. 19
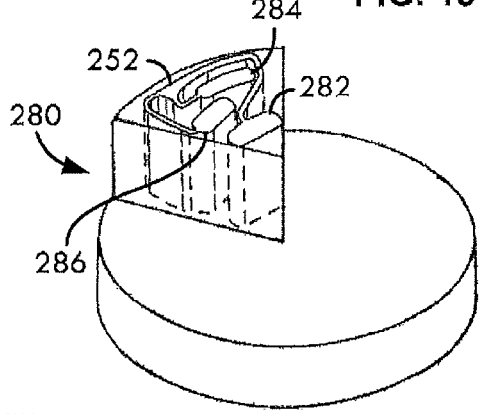
FIG. 20

BLOOD BAG SYSTEMS FOR SEPARATION OF WHOLE BLOOD AND METHODS OF USE THEREOF

CROSS-REFERENCE TO RELATED APPLICATION

This application claims the benefit of U.S. patent application Ser. No. 61/586,985 filed Jan. 16, 2012, which is hereby incorporated herein by reference.

FIELD OF THE DISCLOSURE

The present disclosure relates to systems, apparatus, and methods for processing single units of whole blood.

BACKGROUND

Whole blood is a suspension of particles comprising red blood cells, various types of white blood cells, and platelets, all suspended in plasma. Each component has a therapeutic value and, after collection, units of whole blood are usually separated into individual components. The most common method of separation is to place the unit (container) of whole blood and any associated satellite bags into a receptacle of a centrifuge and spin the centrifuge to separate the blood components into layers. The container (with satellite bags attached) is then removed and introduced into an expresser whereby the separated layers are expressed into the appropriate satellite containers. Fluid transfer often requires the manual opening and closing (e.g., clamping) of different fluid flow paths. This method of removing the container and manually expressing the separated layers to the appropriate satellite containers is both time consuming and labor intensive. Thus, it would be desirable to provide a system and apparatus that eliminates or, at least, simplifies the manual post collection separation and fluid transfer steps. It would also be desireable to perform such separation and fluid transfer steps on multiple units of blood or biological fluid simultaneously.

SUMMARY OF THE DISCLOSURE

Various aspects and embodiments of the present disclosure will become evident in the description that follows. It should be understood that the subject matter of this disclosure, in its broadest sense, can be practiced without having one or more features of the illustrative embodiments. It should also be understood that these aspects and embodiments are merely exemplary. This summary only highlights a few of the aspects of the disclosed subject matter, and additional details are disclosed in the accompanying drawings and more detailed description that follow.

The present disclosure relates generally to systems for processing a unit of whole blood into its components while the unit is still in the centrifuge. The system comprises a container holding whole blood and one or more satellite bags or containers that are installed into a holder, which is then inserted into a bucket of the centrifuge. Tubes interconnect the containers, one or more of which are preferably installed into clamping mechanisms resident in the holder. The holder further preferably includes sensing means, such as optical sensors, to sense the location of the interfaces between the separated layers of the whole blood that result from rotation of the centrifuge.

In keeping with one aspect of the disclosure, a first embodiment of a blood bag system for separation of whole blood into at least two separate blood components with a centrifuge system is provided. The blood bag system comprises a container of whole blood and at least one satellite container. The fluid pathway connects the container of whole blood to the satellite container, with a clamp being associated with the fluid pathway for selectively allowing or preventing flow therethrough. A holder is provided for receipt of the container of whole blood and the satellite container, as well as for receipt of the fluid pathway and the clamp. The holder is configured for mounting to the rotor of a centrifuge for rotation therewith and includes a first receptacle spaced from the axis of rotation of the rotor that receives the container of whole blood and a second receptacle positioned between the container of whole blood and the axis of rotation that receives the satellite container. The holder also includes an actuator for controlling the clamp, and a sensor for determining the location of the interface between two different blood components that are separated as a result of rotation of the rotor, the sensor also controlling the actuator to permit or prevent flow of one of the separated components through the fluid pathway into the satellite container.

In another aspect of the disclosure, a second embodiment of a blood bag system similar to the first embodiment may be provided with a second satellite container, fluid pathway and clamp, and the holder provided with a third receptacle positioned between the axis of rotation and the receptacle that receives the first satellite container to facilitate separation of whole blood into three separate components. The holder is provided with an actuator for controlling the second clamp, with the sensor also controlling the second actuator to permit or prevent flow of one of the separated blood components through the second fluid pathway.

In a further aspect of the disclosure, the blood bag system of the second embodiment may further comprise a bladder associated with the first receptacle of the holder configured to contact the container of whole blood and a second bladder received in one of the second or third receptacles for the satellite containers. A fluid pathway interconnects the first bladder and the second bladder, and the second bladder contains a fluid having a density intermediate the densities of the first and second blood components. Consequently, upon rotation of the rotor, the fluid flows from the second bladder to the first bladder to expand the first bladder into contact with the container of whole blood and to flow a separated blood component from the container of whole blood through the first fluid pathway.

In keeping with another aspect of the disclosure, a third embodiment of a blood bag system is provided comprising first and second deformable containers of whole blood, each container having a volume greater than the volume of whole blood therein, while the volume of blood contained in each of the containers is substantially identical. A holder is provided that is configured for mounting to the rotor of the centrifuge that includes a receptacle for receipt of both the first and second deformable containers of whole blood. The receptacle comprises first, second and third compartments that are positioned sequentially and symmetrically along a radius of the rotor. A relatively narrow channel or passageway separates each of the first compartment from the second compartment and the second compartment from the third compartment. The first, second and third compartments of the receptacle receive the first and second containers of whole blood therein such that the first deformable container of whole blood is received in the receptacles with substantially all of the whole blood contained in the first compartment, and the second deformable container of whole blood is received in the receptacles such that substantially all of the whole blood is contained in the third compartment.

In keeping with another aspect of the third embodiment, the holder preferably includes a sealer and clamp associated with each of the channels that separate the first compartment from the second compartment and the second compartment from the third compartment. Further, the first and second deformable containers may each define three zones corresponding to the compartments of this receptacle, with a sealable flow pathway connecting adjacent zones of the containers. Auxiliary containers may also be connected by fluid flow paths to each of the first and second containers, with the holder having a receptacle for each auxiliary container.

In keeping with another aspect of the disclosure, a fourth embodiment of a blood bag system is provided for separation of whole blood into at least first and second blood components having different densities. A blood bag system comprises a first collection container of whole blood mounted to the rotor of a centrifuge. A second collection container is provided for receipt of the blood component having the higher density, the second collection container being mounted to the rotor at a position radially outward from the first collection container and connected to the first collection container by a first fluid pathway. The first fluid pathway has a valve therein to selectively permit or prevent flow between the first collection container and the second collection container, the first fluid pathway being connected to the first collection container at a radially outward-most position of the first collection container. A third collection container is provided for receipt of the blood component having the lower density, the third collection container being mounted to the rotor at a position radially outward from the first collection container and connected to the first collection container by a second fluid pathway that also includes a valve to selectively permit or prevent flow during the first collection container and the third collection container. The second fluid pathway is connected to the first collection container at a position radially inward from the connection of the first fluid pathway to the first collection container. A free floating member is provided within the first fluid container that is sized to occlude the connection between the first fluid container and the first fluid pathway, with the free floating member having a density intermediate the densities of the first and second blood components.

In another aspect of the disclosure, the fourth embodiment of the blood bag system automatically controls the first and second valves to first permit flow of the higher density blood component through the first fluid pathway into the second collection container until the first fluid pathway is occluded by the free floating member, and then opening the second valve to permit the lower density blood component to flow through the second fluid pathway into the third collection container.

In another aspect of the disclosure, a fifth embodiment of a blood bag system is provided that comprises a container of whole blood and first, second, and third satellite containers with a first fluid pathway connecting the container of whole blood to the first satellite container, a second fluid pathway connecting the first satellite container to the second satellite container through a first port on the first satellite container, and a third fluid pathway connecting the first satellite container to the third satellite container through a second port on the first satellite container. A holder is provided for receipt of the container of whole blood in the first, second, and third satellite containers, with the holder being configured for mounting to the rotor of the centrifuge for rotation therewith. The holder includes a first receptacle spaced from the axis of rotation of the rotor that receives the container of whole blood. A second receptacle is provided for receipt of the first satellite container that is spaced radially outwardly from the first receptacle, and the first satellite container is received in the second receptacle such that the first port is located radially outwardly from the second port. A third receptacle is provided for receipt of the second satellite container that is located radially outward from the second receptacle, and a fourth receptacle is provided for receipt of the third satellite container that is located radially between the first receptacle and the second receptacle.

In another aspect of the disclosure, the second receptacle of the fifth embodiment is formed in the holder along an arc of a spiral having its origin as the axis of rotation of the centrifuge rotor. In addition, valves and sensors may be associated with each of the fluid pathways, as well as a filter.

In another aspect of the disclosure applicable to all embodiments, a plurality of blood bag systems may be associated with a centrifuge rotor to provide for processing of multiple units of whole blood simultaneously.

BRIEF DESCRIPTION OF THE DRAWINGS

It should be understood that the accompanying drawings illustrate only exemplary embodiments of the invention.

FIG. 17 is a schematic plan view of a fifth embodiment of a disposable blood bag system suitable for use in combination with a holder in accordance with the present disclosure.

FIG. 18 is a schematic top view of a centrifuge bucket with a holder for the blood bag system of FIG. 17.

FIG. 19 is an enlarged fragmentary top view of the holder of FIG. 18.

FIG. 20 is a perspective view of the holder of FIGS. 18 and 19 with the centrifuge bucket removed.

DESCRIPTION OF THE PREFERRED EMBODIMENTS

A more detailed description of various embodiments of blood bag systems in accordance with the present disclosure is set forth below. It should be understood that the following description of specific embodiments is meant to be exemplary, and not exhaustive of all possible variations. Thus, the scope of the disclosure is not intended to be limiting, and should be understood to be inclusive of embodiments or variations that would occur to persons of ordinary skill after review of the disclosure.

In a first aspect of the disclosure a unit of blood is allowed to separate into its components (i.e., packed red cells, a buffy coat layer containing many of the white cells and most of the platelets, and a plasma layer substantially free of cellular components). Separation of whole blood into its components is effected by introducing a container of whole blood into a centrifuge device and spinning the centrifuge. In accordance with the present disclosure, the whole blood container is integrally connected to and part of a disposable processing set that includes one or more preattached satellite containers interconnected by tubing providing flow paths for the blood and blood components. The disposable processing set is adapted for placement within or mounted on the centrifuge device of the blood bag system. More particularly, the disposable processing set is adapted to be received by a holder which itself may be placed within or mounted on a centrifuge device. The centrifuge device may accommodate one or more such holders.

Figure 1:
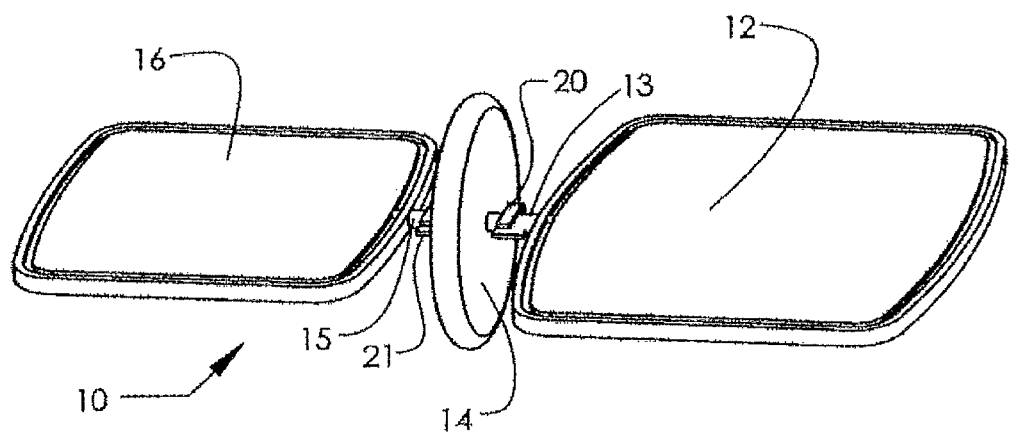
FIG. 1 is a perspective view of a first embodiment of a disposable blood bag system suitable for use in combination with a holder in accordance with the present disclosure.

Turning to FIGS. 1-6, a first embodiment of a blood bag system in accordance with the present disclosure is shown. The system includes a disposable blood pack unit 10 having a main container and one or more satellite containers. More particularly, as shown in FIG. 1, unit 10 includes a whole blood container 12, a first satellite container 14 and second satellite container 16. The whole blood bag 12 is in flow communication with container 14 by tube 13, while the container 14 is in flow communication with container 16 by tube 15. Containers 12, 14, and 16 can be fabricated in any manner and in any shape suitable for use in the present invention by known methods. Herein, whole blood container 12 and container 16 are shown as flat bags with ports at their ends. Container 14 is fabricated as a disk with tubes 13 and 15 positioned approximately in the center of the disk. The disk shape is configured to provide smooth contours for the separated cells to slide upon. However, container 14 may have other shapes without departing from the subject matter of the disclosure. All containers can include additional ports and tubes (not shown) to allow access for other purposes if so desired.

Whole blood container 12 may contain a sufficient amount of anticoagulant (not shown) so that collected blood will not clot. At the time of collection, whole blood is withdrawn from a donor (not shown) into whole blood container 12 through a donor line (also not shown).

In blood collection kits, frangible devices are commonly employed to establish flow communication within the fluid circuit. In another aspect of the present disclosure, the traditional frangible devices installed in the tubing between one container and another in a blood pack may preferably be replaced by clamps, such as clamps 20 and 21 (as described in greater detail below) that are positioned onto tubes 13 and 15, respectively, at the time of manufacture. When installed in the holder (also described below) and in communication with the valving mechanism, the valving mechanism operates against spring loading to open the clamps and allow blood products to flow through the passageway between the containers. The valving mechanism may likewise be activated to close the clamps when fluid transfer is complete. When removed from the holder, the passageways are thus closed, and cross contamination between containers is prevented. The interconnecting tubing can then be sealed by conventional methods, such as radio-frequency welding or the like, and the individual product containers separated for storage or subsequent additional post processing.

Figure 2:
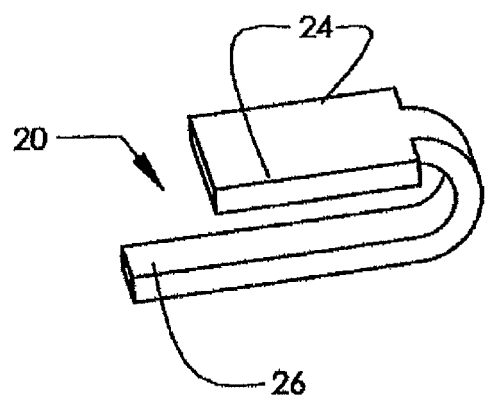
FIG. 2 is a perspective view of a clamp suitable for use in combination with the blood bag system of FIG. 1.
Figure 3:
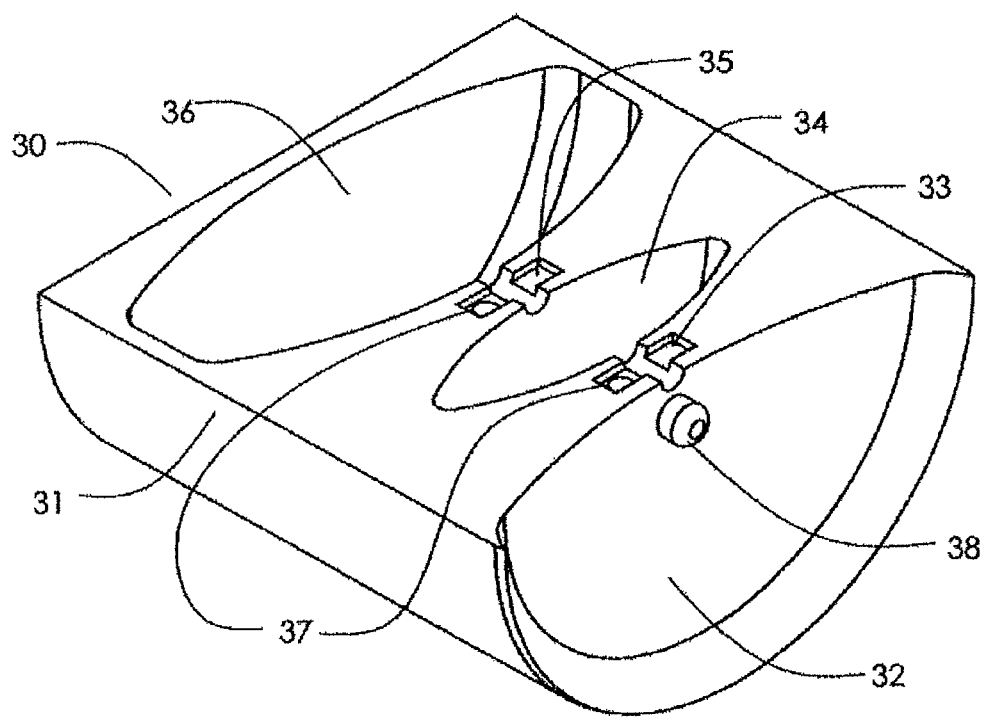
FIG. 3 is a perspective view of a portion of a holder suitable for receiving the blood bag system of FIG. 1.

Referring now to FIG. 2, a specific configuration of clamp 20 comprises a sheet of spring steel bent into a U-shape and having flanges 24 on one side and head 26 on the other. Flanges 24 of the clamps 20, 21 engage an upper half of holder 30 (not shown) while head 26 is preferably engagable by solenoids 37 mounted in holder 30 (as shown in FIG. 3) so that the clamps 20 and 21 can be automatically opened and closed, thus allowing or preventing flow through tubes 13 and 15, as desired. Clamps 20 and 21 are preferably identical and are normally closed.

The lower half of holder 30 is shown in FIG. 3 and comprises block 31 having recesses 34 and 36 adapted to receive containers 14 and 16 respectively. Block 31 further includes wells 33 and 35 to receive clamps 20 and 21 respectively. Wells 33 and 35 further include solenoids 37 to actuate heads 26 of clamps 20 and 21. Block 31 further includes shaped face 32 which may press into whole blood container 12 (or against which whole blood container 12 is pressed). Face 32 includes optical sensor 38. In use, the wall of whole blood bag 12 conforms to sensor 38 and allows sensor 38 to determine the location of, for example, the interface between plasma and the buffy coat, if present, or the packed red cell bed prior to the formation of the buffy coat. When assembled with its mating upper half, holder 30 fits into the bucket of a centrifuge (not shown). The mass of holder 30 can be adjusted so that its weight when rotated at the desired speed will provide a sufficient force on whole blood bag 12 to create enough pressure on the separated plasma therein to allow it to flow as far inwardly as desired. In effect, holder 30 acts like a piston to drive the plasma back towards the center of the rotor.

Figure 4:
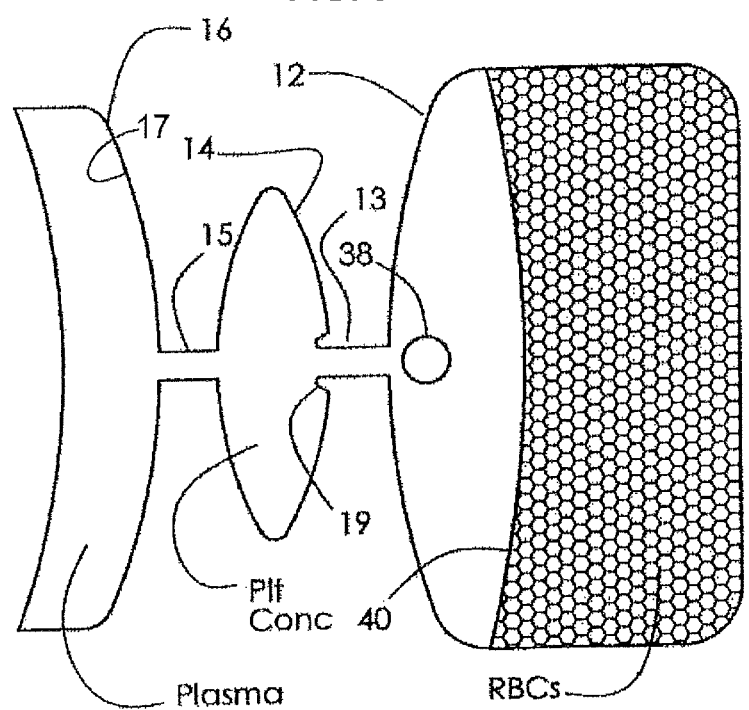
FIG. 4 is a sectioned view of the fluid envelope of the system while in use.

FIG. 4 shows a cross section of whole blood container 12, container 14, and container 16 as they would appear during the centrifugal separation process. Interconnecting tubes 13 and 15 defining flow paths are shown in their open positions. FIG. 4 is shown in top view with the rotor rotating in the plane of the drawing about an axis of rotation located to the left of the figure. Interface 40 located between the red blood cells and plasma is shown part way up whole blood container 12. Optical sensor 38 monitors the location of interface 40 and control clamps 20 and 21, not shown, to maintain interface 40 in a desired location.

In accordance with the disclosure, methods by which the plasma which has been separated from the remainder of the whole blood can be induced to flow from one container to another are provided. As noted above, in one method, the weight of the holder acting on the whole blood unit induces a pressure on the whole blood unit to cause the plasma to flow inwardly. In another method, a fluid-filled bladder may be placed in the bottom of the centrifuge bucket. The bladder can be placed in communication with a reservoir of fluid more inboard than the expected top of the plasma container, either as a part of the centrifuge rotor or with a secondary bladder contained in the holder. In either case, valving can then be effected by controlling the transfer of fluid from the inner bladder to the outer bladder.

In another aspect of the disclosure, a method is provided where the clamping mechanism 20 is actuated shortly after the centrifuge is started and plasma is transferred immediately to satellite container 14. Plasma is transferred immediately upon liberation from the whole blood by activating and de-activating the clamping mechanism 20 in response to signals received from the optical sensor 38. By doing so, platelets in the plasma do not have time to settle to the interface between the red cells and plasma and are, thus, transferred into the satellite container.

In still another aspect of the disclosure, a method is provided where the platelets suspended in the platelet rich plasma are transported through the container 14 and into the container 16, where they are directed onto slanted high-G walls (e.g., wall 17 in FIG. 4 in the plasma container. The separated platelets then slide or tumble down to and back through the passageway 15 between the secondary container 14 and plasma container 16, where they then accumulate in the secondary chamber 14. Thus, there are three component containers at the end of the procedure: one containing red cells (12), one containing platelet concentrate (14), and one containing substantially cell free plasma (16).

More specifically, the plasma expressed into containers 14 and 16 initially contains platelets. The platelets are directed onto the high-G walls of the containers. Those platelets that settle onto the high-G wall of plasma container 16 then slide or "tumble down" the wall where they are directed through tube 15 and then on into secondary container 14 where they join platelets on the high-G wall of container 14. End 19 of tube 13 can extend into container 14 to prevent platelets from dropping back into whole blood bag 12. At the end of the procedure, only packed RBCs remain in whole blood bag 12, container 14 contains platelet concentrate, and container 16 holds plasma. The position of interface 40 is shown in an exaggerated outward position for clarity. In practice, interface 40 would be controlled to reside very near to the high-G end of tube 13.

Another aspect of the disclosure relates to the specific geometry of the above mentioned secondary chamber in that said chamber is constructed as an elutriation stage wherein any stray red cells or white cells fall back through the passageway between the whole blood unit and the secondary chamber while platelets are prevented from doing so by the flow of plasma being transported therethrough from the whole blood unit to the secondary container once the flow rate of plasma has diminished sufficiently.

Specifically, container 14 can be so configured to act as an elutriation chamber specifically designed to leukodeplete the platelet concentrate. While the container 14 is shown having a disk-shape, other shapes may also work for this purpose. The shape of the end of tube 13 as depicted by 19 (FIG. 4) and 19*a* (FIG. 5) can be made a part of the disposable or fabricated into holder 30 with the material of secondary container 14 conforming thereto by pressure.

Figure 5:
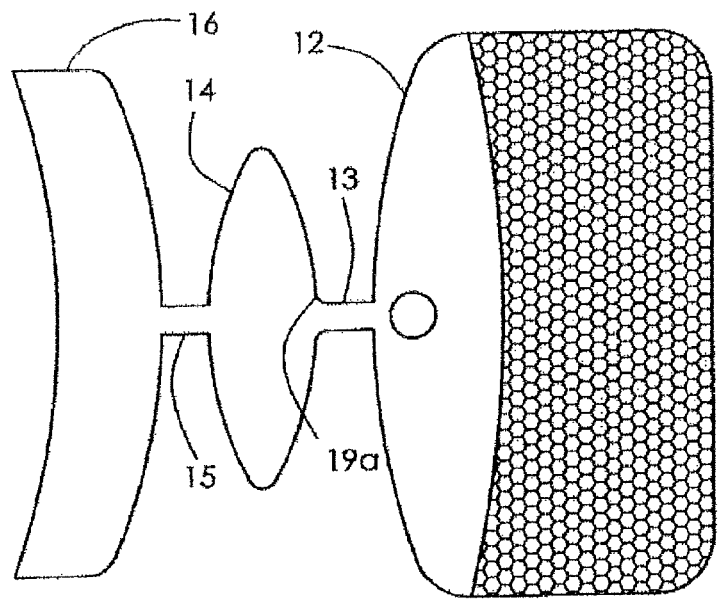
FIG. 5 illustrates an alternate form of the secondary container of the embodiment shown in FIG. 4.

With further reference to FIG. 5, the end 19*a* of tube 13 is shaped to allow platelets to drop back into tube 13, from where they are again transported back into containers 14 and 16. As the flow of plasma from whole blood bag 12 begins to diminish, stray red cells and white cells will begin to fall back into whole blood bag while the much smaller and less dense platelets will be carried with the plasma, thus leukodepleting the platelet product collected.

Once a sufficient number of platelets have been transported out of whole blood container 12 in either the FIG. 4 or FIG. 5 embodiment, tube 13 is closed and all platelets are allowed to fall into secondary container 14. The rotor can continue to spin thereinafter to further pack the red cell bed and clamp 20 can thereafter be opened one more time to allow the resulting additional and virtually cell free plasma to be transported into plasma container 16. Finally, both clamps are closed and the rotor is brought to a stop so that the separated products can be removed from the bucket. Tubes 13 and 15 are then sealed as by radio frequency or the like, and the containers are separated for storage or subsequent additional processing.

In the embodiment of FIGS. 1-6, container 14 preferably holds the majority of the platelets collected during the procedure. It can be fabricated from gas permeable plastic so that the collected platelets can be stored therein until needed for transfusion. Container 14 and well 34 of holder 30 can be designed to have a preselected volume depending upon it intended use. If the platelet concentrate is to be stored in container 14 until used, as is common practice in the United States, then a typical volume would be on the order of 50 ml. Alternatively, if the platelet concentrate is to be immediately pooled with several other platelet concentrates and diluted with a platelet additive solution for storage, as is the practice in many parts of Europe, then a volume of 15 to 20 ml would be appropriate.

Figure 6:
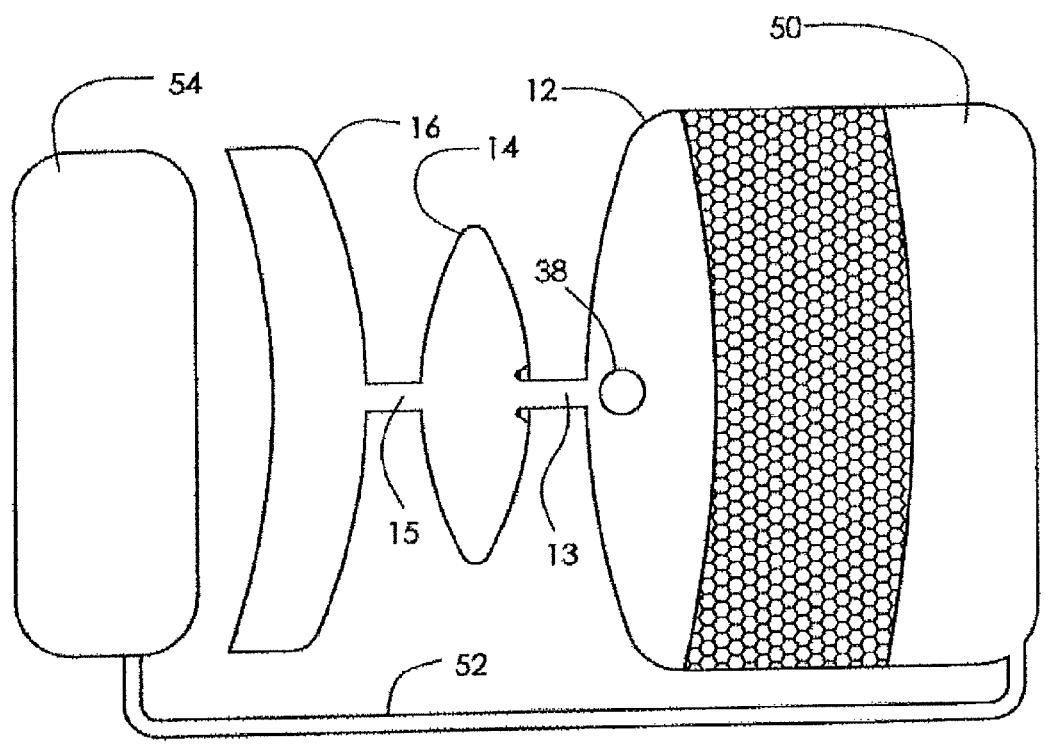
FIG. 6 is a schematic view of fluid-filled bladders suitable for use as an alternate means to affect the transfer.
Figure 7:
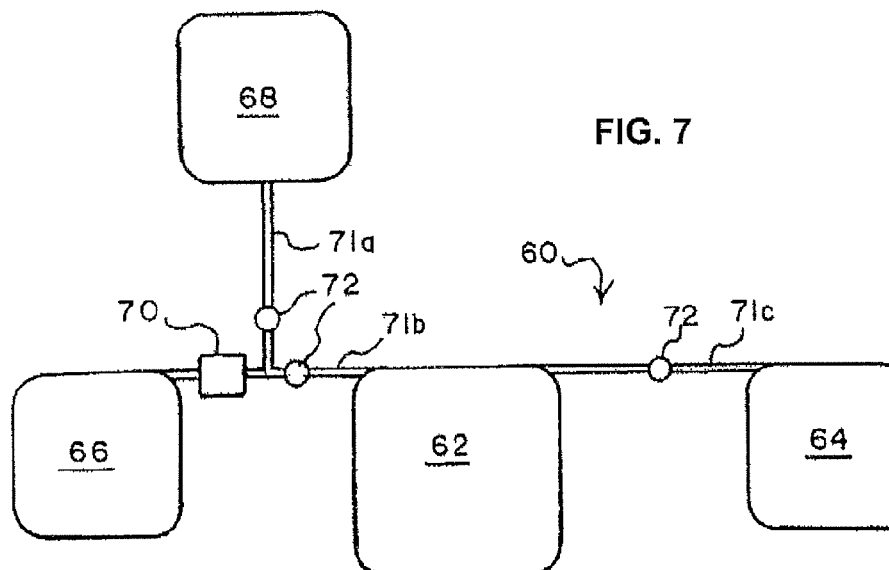
FIG. 7 is a schematic plan view of a second embodiment of a disposable blood bag system suitable for use in combination with a holder in accordance with the present disclosure.
Figure 8:
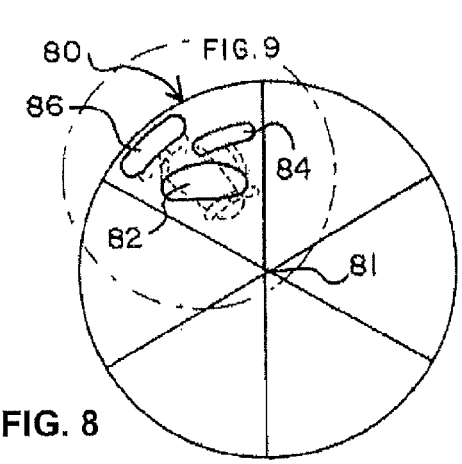
FIG. 8 is a schematic top view of a centrifuge bucket with a holder for the blood bag system of FIG. 7.
Figure 9:
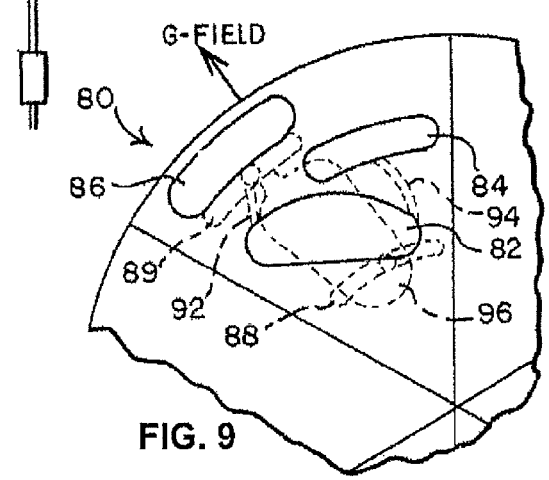
FIG. 9 is an enlarged fragmentary top view of the holder of FIG. 8.
Figure 10:
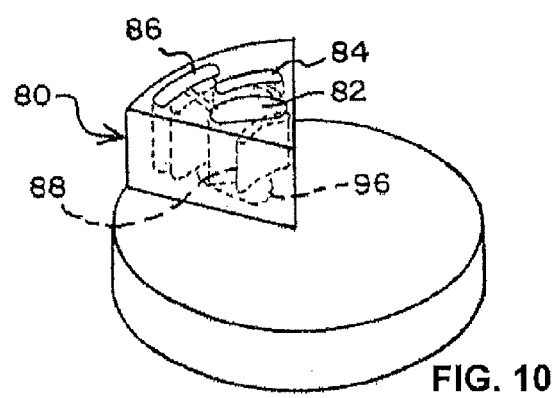
FIG. 10 is a perspective view of the holder of FIGS. 8 and 9 with the centrifuge bucket removed.

FIG. 6 shows an alternate configuration of a blood bag system and a method by which plasma may be pumped from whole blood container 12 to containers 14 and 16. As shown in FIG. 6, Bladder 50 is in contact with the whole blood container 12 and is a separate container located in the bottom of the centrifuge bucket before whole blood container 12 and the holder assembly comprising both halves of holder 30 and containers 14 and 16 are installed. Bladder 50 is connected to a second bladder 54 by tube 52. Bladder 50 is initially empty while bladder 54 contains a fluid having a density higher than that of packed cells, such as, but not limited to, ethylene glycol. Holder 30 is coupled to the centrifuge bucket in locked engagement. Once the rotor is set into motion, the hydrostatic pressure induced in bladder 50 as fluid flows from bladder 54 into bladder 50 displaces the liberated plasma from whole blood container 12 into containers 14 and 16. The flow can be controlled by clamping and releasing tubes 13 and 15, as in the prior embodiments discussed above, or an additional clamp can be used on tube 52 to control the rate and magnitude of transfer in response to signals received from optical interface sensor 38. Alternatively, bladder 54 can be eliminated by providing a source of fluid outside the rotor and in communication with bladder 50 through, e.g., a rotating seal in the shaft of the rotor (not shown).

In the embodiments of FIGS. 1-6, plasma flows into secondary container 14. Alternatively, part or all of the buffy coat can be expressed into secondary container 14 if so desired.

Frequently, blood packs include additional components such as red cell storage solutions and filters. Although not shown in the figures, these components can also be included in the disposable shown in FIG. 1, and holder 30 can include additional valving mechanisms and sensors to allow their use in the system.

It will be appreciated that air is usually introduced and present in blood pack 10 and, more particularly, in plasma container 16. It is frequently desired that that air be expressed out of the container prior to storage or freezing. Thus, in one embodiment, blood pack 10 can include an additional container or the like still more inboard to receive that air. Alternatively, plasma container 16 can include a sterile barrier filter to pass the air directly into the atmosphere.

The embodiments of FIGS. 1-6 have been depicted in a form that allows the collection of three components. It is to be understood that secondary container 14 can be eliminated when only packed red blood cells and plasma are to be collected. In such a system, transferring plasma from the whole blood container 12 to plasma container 16 can also be delayed until the end of the procedure wherein the plasma is virtually cell free.

Turning to FIGS. 7-10, a second embodiment is shown that provides a blood bag system for the separation and automatic expression of blood and blood components by a centrifuge system. The system may be used for either two component or three component processing of whole blood.

The disposable portion 60 of the blood bag system preferably comprises a donor or vascular access portion 63 with a sampling system, a collection container or separation container 62 for the receipt of whole blood, a first satellite container 64 for the receipt of a separated plasma product, and a second satellite container 66 for the receipt of a RBC product. If the system is to be used for three component processing, a third satellite container 68 for the receipt of buffy coat is also provided. Fluid pathways between the respective satellite containers and the container of whole blood are provided by tubings or conduits 71a, 71b, 71c. A filter, such as a leukoreduction filter 70, may be preferably interposed in the fluid pathway 71b between the collection container 62 of whole blood and the second satellite container 66 for receipt of the RBC product.

The blood bag system further comprises a holder or centrifuge cup 80 having a series of compartments or receptacles configured to receive the various containers of the disposable blood bag system. The holder 80 is inserted into or otherwise mounted to the rotor of a centrifuge so as to rotate about axis 81. A first receptacle or compartment 82 is provided in the holder 80 that receives the collection container 62 of whole blood. A second receptacle or compartment 84 is located radially outwardly from the compartment 82 for the whole blood container for receipt of the first satellite collection container 64 for the plasma product, and a third receptacle or compartment 86 is located radially outwardly from the second receptacle 84 for receipt of the second satellite container 66 for the RBC product. The holder 80 is also provided with recesses for receiving valves and sensors 72 to control the flow from the container of whole blood to the satellite containers. The holder 80 may also include dedicated space to hold plasma and RBC filters (not shown). Preferably, the valves 72 are configured to also seal the product bags at the end of the procedure.

The first compartment 82 includes first and second ports 92, 94, respectively, to facilitate the loading of the disposable bag system into the holder. The RBC port 92 is located radially outwardly relative to the plasma port 94. Preferably, the center line of the separation compartment 82 lies on a spiral in the G-field.

The RBC compartment 86 and plasma compartment 84 in holder 80 are located in the G-field to enhance the product separation and to restrict the flow of packed RBC and plasma into their respective satellite containers. Hydraulic bladders, 88, 89, as described above, may be present near or at the inner walls of the compartments 82, 86 (for the whole blood container and the RBC) to restrict or control the flow of RBC and plasma to their respective satellite containers. The bladders preferably are in fluid communication with a central reservoir 96 that provides a single hydrostatic reference pressure. The bladders 88, 89 also preferably automatically drain into the reservoir 96 when the centrifuge is at rest in order to facilitate loading.

Hydraulic bladders 88, 89 provide a continuous pressure gradient from the second satellite container 66 for the RBC to the innermost portion of the separation chamber 82 that receives the container 62 of whole blood. While the hydraulic bladders provide for greater control, they are optional, and the energy for expressing or flowing the separated components into their respective satellite containers can be created by the appropriate positioning of the product receptacles in the G-field, and the control of the rotational speed of the centrifuge. As the centrifuge slows, a valve 72 associated with the flow path 71c between the first satellite container 64 for the plasma can be cycled to provide automatic air expression from the plasma product container back to the separation chamber 62.

Figure 11:
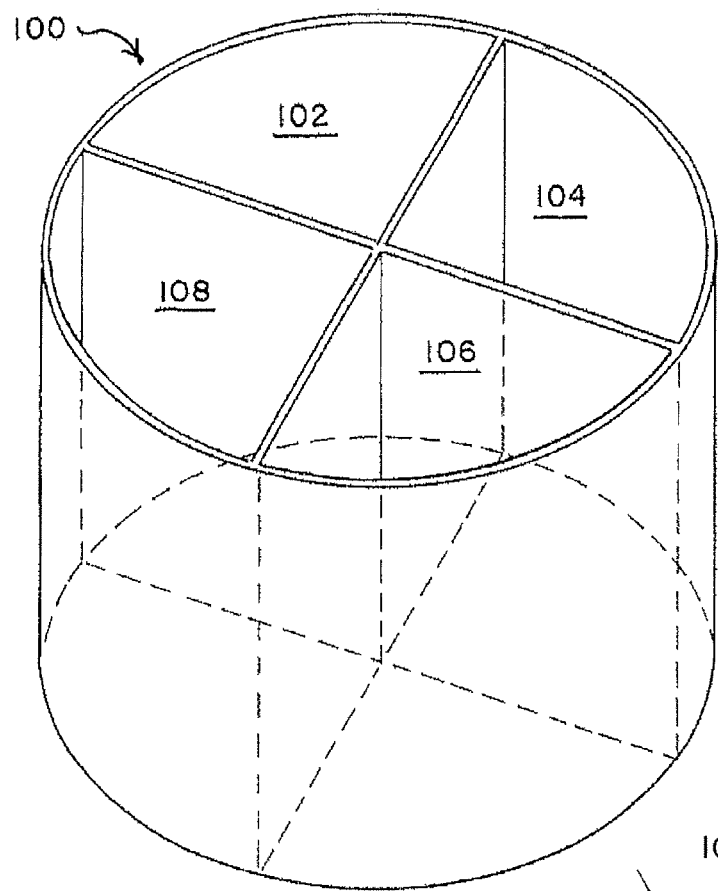
FIG. 11 is a perspective view of a centrifuge bucket suitable for receiving a holder in accordance with a third embodiment in accordance with the present disclosure.
Figure 12:
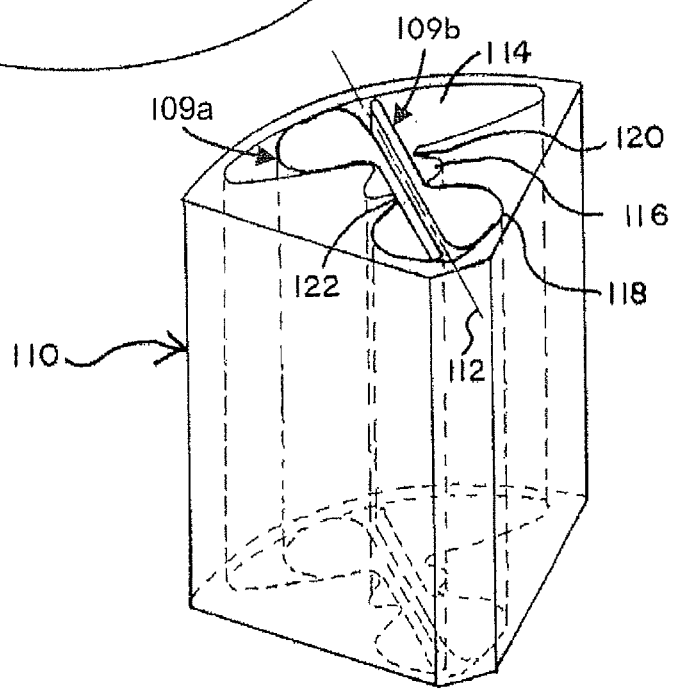
FIG. 12 is a perspective view of a blood bag system and holder in accordance with a third embodiment.

In a further aspect of the disclosure, the separation of whole blood may be accomplished by way of competing fluids within a confined space and centrifugal field. Turning to FIGS. 11 and 12, a holder or cartridge 110 is configured to be received in the centrifuge 100. In this embodiment, the cartridge 110 is loaded with two whole blood collection containers, 109a, 109b within a single receptacle in the cartridge, the receptacle defining three compartments 114, 116, 118. The whole blood in each collection container 109a, 109b is preferably of similar volume and hematocrit. The first container 109a of blood is loaded with the blood contents residing in compartment 114, which is located at the largest centrifugal radius, while the second bag 109b is loaded so that the blood therein is contained in compartment 118, which is located at the smallest centrifugal radius. The walls of the two containers of blood 109a, 109b are in direct contact with each other and confined to occupying the same space in each of the three rigid chambers 114, 116, 118 in the holder so as to be positioned generally on opposite sides of a centerline 112 through the three compartments and causing the containers 109a, 109b to each define a first, radially innermost zone, a second, intermediate zone and a third, radially outermost zone corresponding to the compartments 118, 116, and 114, respectively.

Once a sufficient centrifugal force is attained over the area of the two bags of blood, the red blood cells and other cellular components contained in the first bag 109a start to move toward the wall with the greatest centrifugal force (i.e., the high G wall), forcing plasma to separate and move in the first bag toward other compartments 116, 118 in the cartridge 110 that have lower centrifugal forces. The second blood bag 109b starts with the whole blood in the compartment 118 with the lowest centrifugal forces, forcing the red blood cells to move out of that compartment, through compartment 116, and into the compartment 114 with the highest centrifugal forces. This movement of the separating blood components in each of the two blood bags results in the two fluids competing for space and forcing the other fluid to stratify in the three compartments.

Once the blood components are separated within the bags 109a, 109b into the three compartments 114, 116, 118 of the cartridge 110, the areas of the blood bags containing the separated components may then be sealed from each other and further processing can take place. If there is a need for filtering of the blood, for example, leukocyte filtering, it may be done by way of opening necessary fluid pathways and taking advantage of existing centrifugal forces to route fluid to the proper locations.

The disposable whole blood pack 109a or 109b may be a specialized bag used for the collection of anticoagulated whole blood and the automated separation and expression of the whole blood into blood components. Preferably, the shape of the bag is such that there are three compartments separated by sealable flow pathways. The first and the third chamber are very similar in volume, while the third center chamber is significantly smaller and used for receipt of intermittent density components. The other two chambers, once separation and expression have taken place, will contain either red blood cells or plasma.

The three compartments 114, 116, 118 of the cartridge 110 are connected to each other by two passages 120, 122. The three compartments and two passages work together with the specialized bags to provide for the separation and expression of the whole blood. The compartments are coupled in such a way to ensure the chambers of the bags stay in their respective rigid compartments when the maximum centrifugal force is applied.

The rigid components 110 of this separation device are designed to integrate with commercially available centrifuges. The cartridge 110 is balanced within the centrifuge 100 by an opposing weight or identical cartridge received in one of the buckets 102, 104, 106, 108 on the opposite side of the axis of rotation, resulting in the possibility of having a plurality evenly balanced cartridges inside of one centrifuge, depending on available area. The rigid cartridge has locators for all the necessary disposable components required for a particular type of whole blood processing. These components may include things such as additive solutions (i.e., Adsol) and/or different types of blood filters and any associated tubing.

Turning to FIGS. 13-16, a further embodiment of a blood bag system 150 suitable for two component separation is provided. The system 150 comprises a first collection container 154 of whole blood, a second collection container 156 for receipt of the blood component having the higher density (i.e., RBCs), and a third collection container 158 for receipt of the blood component having the lower density (i.e., plasma). The blood bag system 150 is configured to be mounted within a rotor compartment of a centrifuge system for rotation about an axis 152 such that the collection container for the blood component having the higher density (the second collection container 156) is mounted radially outwardly from the container 154 of whole blood, while the collection container for the blood component having the lower density (the third collection container 158) is mounted to the rotor radially outwardly from the whole blood container 154. System 150 includes a fluid pathway 166 connected to the whole blood container 154 at a position 172 radially inward from the connection point for the fluid pathway 160 between the whole blood container 154 and the collection container 156 for the receipt of the blood component having the higher density.

Figure 14:
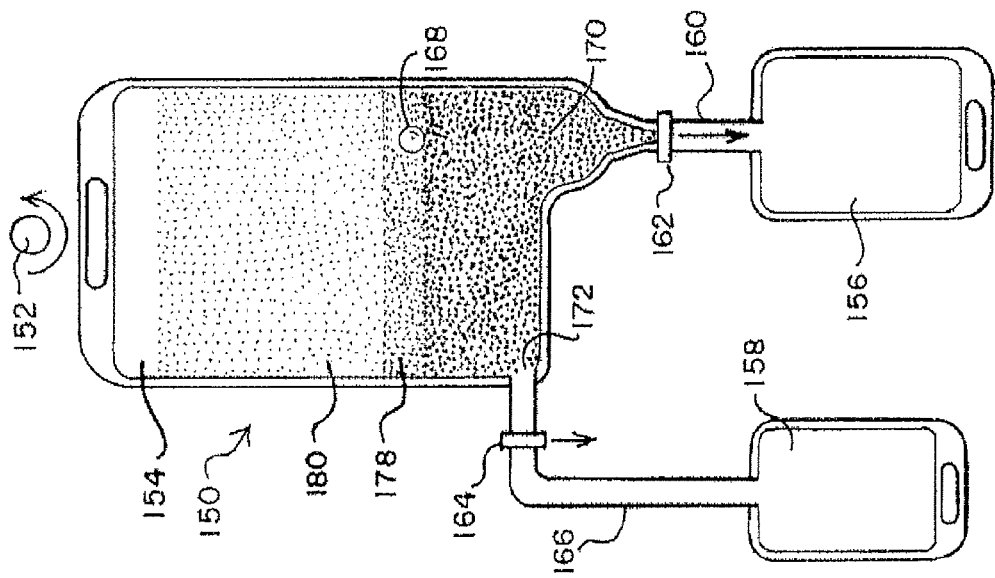
FIGS. 13-16 are schematic plan views of a blood bag system in accordance with a fourth embodiment of the disclosure.
Figure 13:
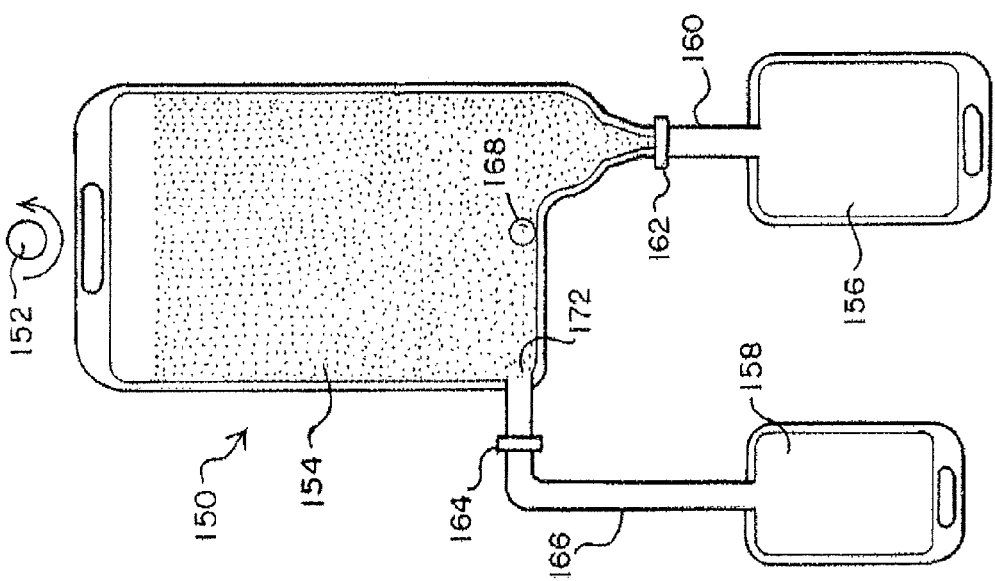
Figure 16:
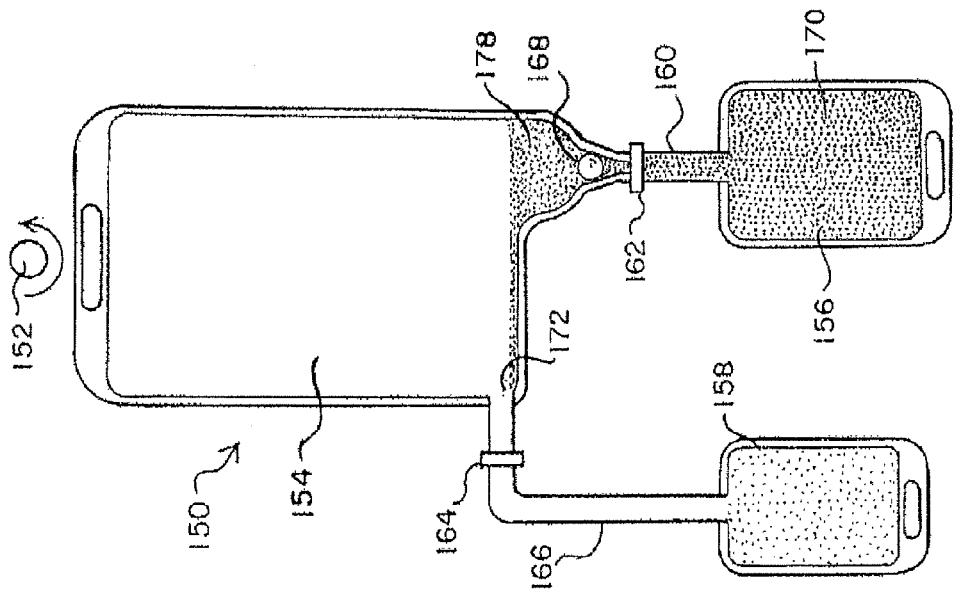
Figure 15:
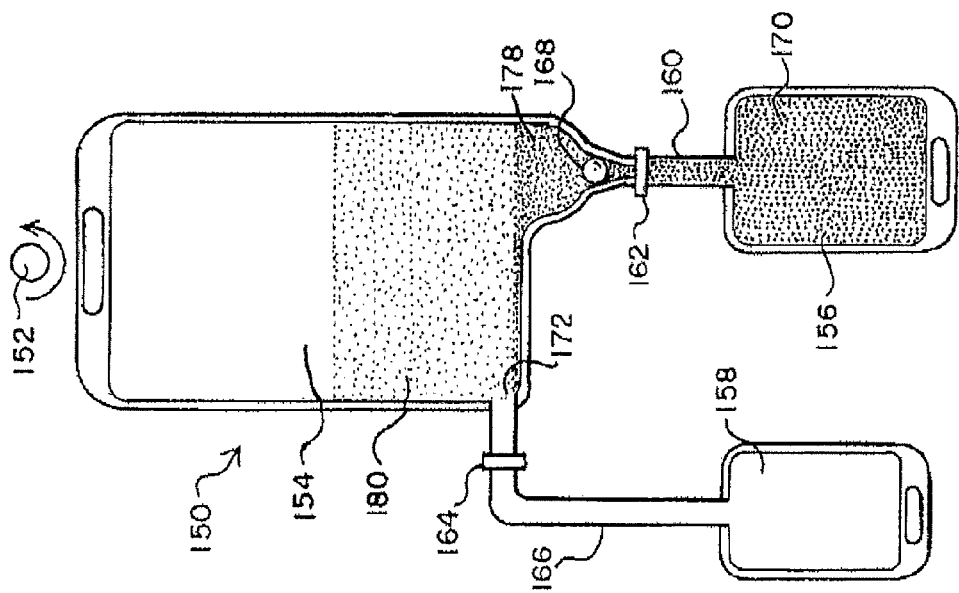

Container 154 for the whole blood is provided with a free-floating member 168 that is sized to occlude the connection between the whole blood container 154 and the fluid pathway 160 to the RBC collection container 156, with the free-floating member 168, having a density intermediate the densities of buffy coat and RBC. Thus, once the whole blood has been centrifuged to separate it into its components, namely RBCs 170, buffy coat 178, and plasma 180 (as seen in FIG. 14), the first valve 162 between the whole blood collection container 154 and the RBC container 156 is opened to allow RBCs 170 to be expressed out of the whole blood container 154 through fluid pathway 160 and into the RBC container 156. As the RBCs 170 get completely expressed out of the whole blood container 154, the density ball 168 occludes the pathway, and the flow through the pathway 160 is stopped (as seen in FIG. 15). The first valve 162 may then be closed to seal the RBC collection container 156. The second valve 164 between the whole blood collection container 154 and the plasma container 150 may then be opened and the plasma 180 expressed out of the whole blood collection container 150 through fluid pathway 166 and into the plasma container 158, leaving the buffy coat 178 in the whole blood collection container 154 (as seen in FIG. 16). As discussed in connection with various of the other embodiments, filters and sensors may be employed in the flow paths between the whole blood container and the satellite containers to provide for greater functionality and more precise operation.

Turning to FIGS. 17-20, a further embodiment of a blood bag system similar to that shown in FIGS. 7-10 is provided in which the disposable portion 260 includes an additional satellite container 250. (In the description that follows, the various components of the embodiment of FIGS. 17-20 that are common to the embodiment of FIGS. 7-10 will be designated by a reference number starting with 2 in the "hundreds" place, and having the same numbers in the "tens" and "ones" places.) The additional satellite container 250 forms a continuous flow separation device into which the whole blood flows before it is separated into components that are directed to the satellite containers 264, 266 for receipt of the plasma and RBC respectively. The holder 280 consequently additionally includes a receptacle 252 for receipt of the continuous flow separation device 250, the receptacle 252 being radially outward of both of the receptacles 286, 284 for the RBC container 266 and plasma container 264. The receptacle 252 for the continuous flow separation device 250 is formed in the holder 280 along an arc of a spiral.

The continuous flow separation device 250 includes a fluid pathway 254 connecting it to the container of whole blood 262, and further includes two outlets 256, 258 through which the separated RBCs and plasma flow to their respective containers. The port 256 for the RBCs is located radially outwardly from the port 258 for the plasma. As with the embodiment of FIGS. 7-10, filters, valves and sensors may be associated with the various fluid pathways and bladders with the receptacles to regulate flow between the various containers.

All of the various embodiments of blood bag systems set forth in this disclosure have been illustrated in singular form. However, multiple units of blood could be processed in a single centrifuge rotor at the same time by mounting a plurality of such blood bag systems to the rotor. Many existing rotors can process six units at a time, thus saving time and labor. Electrical power can be coupled into any number of holders to power sensors and solenoids through slip rings in the rotor. Alternatively, battery packs can be employed for use in systems adapted for existing rotors.

Thus, improved systems for processing units of whole blood into its various components with a centrifuge have been disclosed. The descriptions provided above are intended for illustrative purposes only and are not intended to limit the scope of the disclosure to any particular embodiment described herein. As would be obvious to those skilled in the art, changes and modifications may be made without departing from the disclosure in its broader aspects.

The invention claimed is:

1. A blood bag system for separation of whole blood into at least two separate blood components with a centrifuge system comprising a rotor rotatable about an axis of rotation, the blood bag system comprising:
   a first deformable container of whole blood, the first container having a volume greater than the volume of whole blood therein;
   a second deformable container of whole blood, the second container having a volume greater than the volume of whole blood therein;
   the first and second containers and the volume of blood contained therein being substantially identical;
   a holder being configured for mounting to the rotor of the centrifuge for rotation therewith, the holder having a receptacle comprising first, second and third compartments positioned sequentially and symmetrically about a radius of the rotor with a relatively narrow channel separating each of the first compartment from the second compartment and the second compartment from the third compartment, the first, second and third compartments receiving the first and second containers therein with the first deformable container of whole blood being received in the receptacle such that substantially all of the whole blood is contained in the first compartment and the second deformable container of whole blood being received in the receptacle such that substantially all of the whole blood contained is contained in the third compartment of the receptacle.

2. The blood bag system of claim 1 wherein the holder includes a sealer and clamp associated with each of the channels separating the first compartment from the second compartment and the second compartment from the third compartment.

3. The blood bag system of claim 1 wherein the first and second deformable containers each define three zones corresponding to the compartments of the receptacle with a sealable flow pathway connecting adjacent zones of the containers.

4. The blood bag system of claim 3 wherein the radially innermost and radially outermost zones of each deformable container are of substantially the same volume and the intermediate zone has a volume smaller than that of the innermost and outermost zones.

5. The blood bag system of claim 1 wherein each of the first and second deformable containers comprises one or more e auxiliary containers connected by a fluid flow path to each of the first and second containers, the holder having a receptacle for each auxiliary container.

6. A centrifuge system comprising:
 a first deformable container of whole blood, the first container having a volume greater than the volume of whole blood therein;
 a second deformable container of whole blood, the second container having a volume eater than the volume of hole blood therein;
the first and second containers and the volume of blood contained therein being substantially identical;
 a rotor rotatable about an axis of rotation; and
 a holder configured for mounting to the rotor of the centrifuge for rotation therewith, the holder having a receptacle comprising first, second and third compartments positioned sequentially and symmetrically about a radius of the rotor with a relatively narrow channel separating each of the first compartment from the second compartment and the second compartment from the third compartment, the first, second and third compartments receiving the first and second containers therein with the first deformable container of whole blood being received in the receptacle such that substantially all of the whole blood is contained in the first compartment and the second deformable container of whole blood being received in the receptacle such that substantially all of the whole blood contained is contained in the third compartment of the receptacle.

7. The centrifuge system of claim 6 wherein the holder includes a sealer and clamp associated with each of the channels separating the first compartment from the second compartment and the second compartment from the third compartment.

8. The centrifuge system of claim 6 further comprising a blood bag system with first and second deformable containers wherein the first and second deformable containers each define a radially innermost zone, an intermediate zone, and a radially outermost zone corresponding to the compartments of the receptacle, with a sealable flow pathway connecting adjacent zones of the containers.

9. The centrifuge system of claim 8 wherein the radially innermost and radially outermost zones of each deformable container are of substantially the same volume and the intermediate zone has a volume smaller than that of the innermost and outermost zones.

10. A method for centrifugal separation of whole blood into at least two separate blood components with a centrifuge system comprising a rotor rotatable about an axis of rotation and a holder mounted to the rotor of the centrifuge for rotation therewith, the holder having a receptacle comprising first radially-innermost compartment, a second intermediate compartment, and a third radially-outermost compartment positioned symmetrically about a radius of the rotor, with a relatively narrow channel separating each of the first compartment from the second compartment and the second compartment from the third compartment, a first deformable container of whole blood, the first container having a volume greater than the volume of whole blood therein, and a second deformable container of whole blood, the second container having a volume greater than the volume of whole blood therein, the first and second containers and the volume of blood contained therein being substantially identical, the method comprising:
 placing the first and second containers into the first, second and third compartments in contact with each other, with the first deformable container of whole blood being received in the receptacle such that substantially all of the whole blood is contained in the first radially-innermost compartment and the second deformable container of whole blood being received in the receptacle such that substantially all of the whole blood contained is contained in the third radially-outermost compartment of the receptacle;
 rotating the rotor of the centrifuge system to subject the contents of the first and second containers to a centrifugal force such that blood components in the first container having a relatively higher density move toward the third radially-outermost compartment to displace the blood components in the second container having a relatively lower density toward the first radially-innermost container; and
 sealing the blood bags in the regions of the narrow channels after stratifying the blood components by density into one of the three compartments.

* * * * *